(12) United States Patent
Ström

(10) Patent No.: US 6,840,241 B2
(45) Date of Patent: Jan. 11, 2005

(54) APPARATUS FOR DETERMINATION OF RECRUITABLE VOLUME OF A LUNG

(75) Inventor: Christer Ström, Piteå (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/665,777

(22) Filed: Sep. 19, 2003

(65) Prior Publication Data

US 2004/0055599 A1 Mar. 25, 2004

(30) Foreign Application Priority Data

Sep. 25, 2002 (SE) .............................................. 0202831

(51) Int. Cl.$^7$ .............................................. A61M 16/00
(52) U.S. Cl. ............................ 128/204.21; 128/204.23; 128/207.14
(58) Field of Search ........................ 128/204.21, 204.23, 128/204.25, 205.24, 207.14, 207.15; 600/529, 532, 533, 538

(56) References Cited

U.S. PATENT DOCUMENTS

| 5,937,854 A | 8/1999 | Stenzler |
| 6,116,241 A | 9/2000 | Huygen et al. |
| 6,390,092 B1 | 5/2002 | Leenhoven |

FOREIGN PATENT DOCUMENTS

| EP | 0 745 402 A1 | 12/1996 |
| EP | 1 108 391 A2 | 6/2001 |
| EP | 1 295 620 A1 | 3/2003 |
| WO | WO 00/33733 A1 | 6/2000 |
| WO | WO 01/68162 A2 | 9/2001 |

OTHER PUBLICATIONS

"A Comprehensive Equation For The Pulmonary Pressure–Volume Curve," Venegas et al, J. of App. Physiology, vol. 84 (1998), pp. 389–395.

"Alveolar Derecruitment at Decremental Positive End–Expiratory Pressure Levels in Acute Lung Injury," Maggiore et al, Am. J. of Respiratory and Critical Care Medicine, vol. 164, No. 5 (Sep. 1, 2001), pp. 795–801.

"Pressure–Volume Curve and Alveolar Recruitment in the Course of Acute Respiratory Syndrome," Richard etal, Reéanimation, vol. 10 (2001), pp. 16–20.

*Primary Examiner*—Henry Bennett
*Assistant Examiner*—Andrea M. Ragonese
(74) *Attorney, Agent, or Firm*—Schiff Hardin LLP

(57) ABSTRACT

An apparatus for determination of a recruitable volume in a lung has a control system connectable to a pneumatic unit and to a measurement system and operable to, at a first point in time, regulate the pneumatic unit to generate a first test breath having predetermined parameters with respect to flow and/or pressure of the gas flow, register volume and pressure in the lung during the first test breath, measured by the measurement system. The control system is at a operable second point in time, to regulate the pneumatic unit to generate a second test breath identical to the first test breath, register volume and pressure in the lung during the second test breath, measured by the measurement system. The control system compares the registered volume and pressure for the first test breath and the second test breath, and determines a recruitable volume based on the comparison.

2 Claims, 2 Drawing Sheets

APPARATUS FOR DETERMINATION OF RECRUITABLE VOLUME OF A LUNG

BACKGROUND OF THE INVENTION

1. Field of the Invention

The present invention relates to an apparatus for determination of recruitable volume of a lung.

2. Description of the Prior Art

Mechanical ventilation of lungs is frequently used as a life saving and life supporting measure. At the same time, mechanical ventilation may contribute to the worsening of existing disease conditions and even cause damage to the lungs if sufficient dynamical and physiological considerations are not made when the ventilation parameters are determined. It should be noted that some damage may be unavoidable in the process of saving or maintaining life of a patient. "Patient" is here and henceforth intended to include all lung-respirating animals, including humans.

One inherent property of a lung is its tendency to collapse. For the healthy lung this tendency is countered by the chest and a natural substance, surfactant, in the lungs. Under certain disease conditions the tendency to collapse is increased and portions of the lung will collapse at an early stage during exhalation and open at a late stage during inhalation. Portions of the lung may even stiffen completely and become atelectatic.

One way of preventing collapse is to provide a Positive End Expiratory Pressure (PEEP) during the mechanical ventilation. In order to obtain the best effect of PEEP, the lung should first be opened as much as possible. This is done through a recruiting breath. Relatively high pressures can be required to open a fully or partially collapsed lung.

However, the relation between ventilation/perfusion (gas exchange between the lung and the blood (circulatory system)) can fluctuate widely in a diseased or damaged lung. Therefore, a collapse may occur due to uptake of gas from a part of the lung (specifically singular alveolus or clusters of alveoli) to the blood system without being replaced by ventilation. This may especially occur during monotonous mechanical ventilation of the lung.

It is therefore desirable to gather information that may assist a physician in determining how a treated lung develops after recruitment or during treatment. Information regarding volume-related development is of particular interest. A partially collapsed lung may be in need for instance, of a new recruitment breath.

SUMMARY OF THE INVENTION

An object of the present invention is to provide an apparatus for determination of recruitable volume of a lung, which provides the desired information.

This object is achieved in accordance with the invention in an apparatus for determining the recruitable volume in a lung, having a control system, a pneumatic system that supplies breathing gas to a respirating subject, and a measurement system, wherein the control system, at a first point in time, regulates the pneumatic system to generate a first test breath having predetermined parameters with respect to at least one of flow and pressure of the breathing gas, and registers volume and pressure in the lung during the first test breath, as measured by the measurement system, and wherein the control system, at a second point in time, regulaters the pneumatic unit to generate a second test breath identical to the first test breath, and registers volume and pressure in the lung during the second test breath, as measured by the measurement system, and wherein the control system compares the registered volume and pressure for each of the first and second test breaths and determines the recruitable volume based on the comparison.

The apparatus can be connected to a pneumatic unit for generating a flow of gas to the patient. The pneumatic unit can in principle be a known respirator/ventilator manufactured for this purpose. In its simplest design the pneumatic unit may have a valve for regulating the gas from a gas source. The gas source may be a high pressure network, a compressor, a fan or other gas source. The pneumatic unit may of course be integrated with the apparatus.

A measurement system for determining volume and pressure may in one embodiment includes a flow meter and a pressure meter for the gas flow from the pneumatic unit. An estimation or calculation of the gas volume to the lung with respect to gas pressure in the lung can be made based on known mathematical equations for compensating pressure drop in tubes, etc. In a more advanced measurement system, flow meters and pressure meters can be arranged in direct connection with the lung, e.g. at the lower end of a tracheal tube. A number of suitable measurement systems are known.

If an existing respirator/ventilator forms the pneumatic unit, existing meters for flow/volume/pressure in the respirator/ventilator can be utilized as the measurement system.

The control system forms the most vital part of the apparatus. If an existing respirator/ventilator is utilized, a part of its control and regulating system can be utilized as part of the inventive control system.

The essential function for the control system according the invention is to determine the recruitable volume in the lung at specific time intervals and determine a trend for the changes in recruitable volume during certain treatment. The time intervals can be fixed time intervals or can be related to a specific number of breaths or some other suitable parameter.

Briefly, the recruitable volume is defined as a difference between two pressure-volume curves obtained using the same breath parameter at different times. Normally, portions of the lung will start to collapse again after a recruitment maneuver so the recruitable volume dictates a loss of ventilated volume as a rule. The reverse may also occur, i.e. a treatment leads to the opening of previously collapsed regions. In the latter case a negative recruitable volume is obtained as a result of the determination made by the inventive apparatus.

DESCRIPTION OF THE PREFERRED EMBODIMENTS

Figure 1:
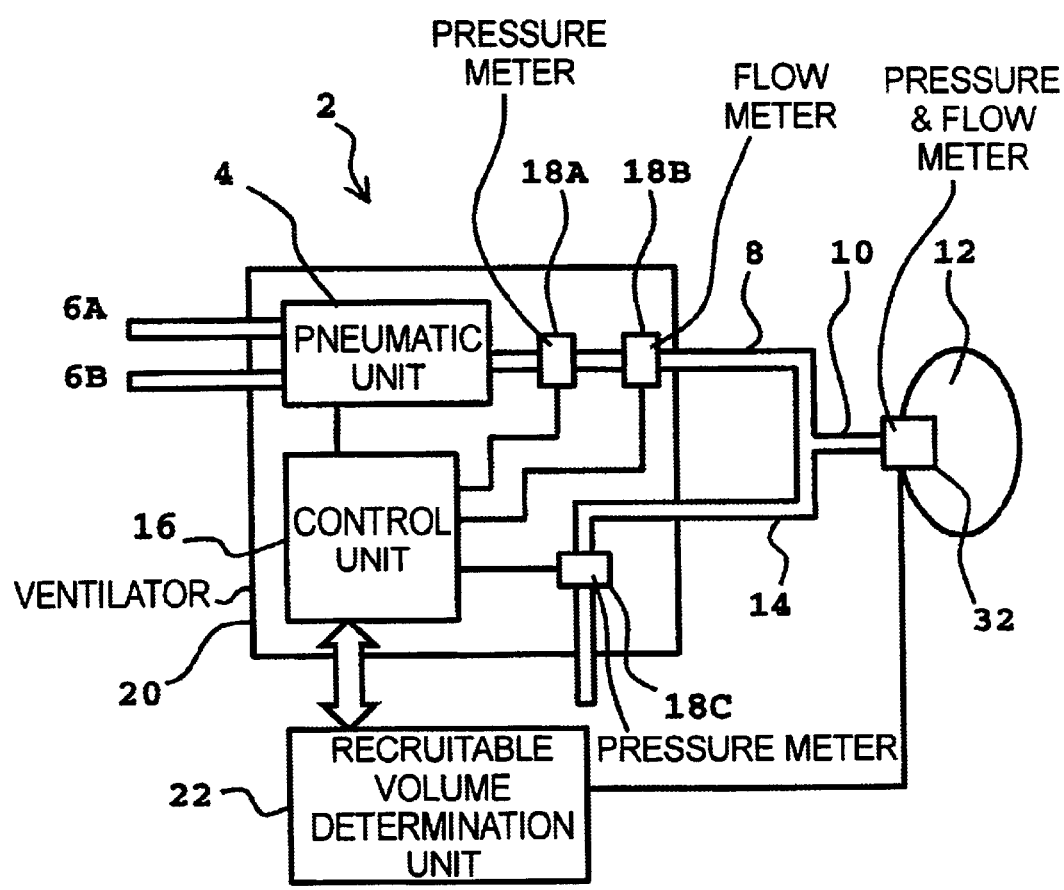
FIG. 1 is a block diagram of an embodiment of an apparatus according to the invention, connected to a ventilator.

In FIG. 1 a ventilator system 2 is shown. The ventilator system 2 has a pneumatic unit 4 which via gas inlets 6A, 6B, receives gases to mix and regulate a respiratory gas.

The respiratory gas is supplied to a patient 12 via an inspiration tube 8 and patient connector 10. The respiratory gas is conducted from the patient 12 via an expiration tube 14.

A control unit 16 controls the pneumatic unit 4. A measurement system having a first pressure meter 18A, a flow meter 18B and a second pressure meter 18C provides the control unit 16 with measurement data regarding pressure and flow of the respiratory gas. From the flow, the volume can be calculated in a known manner.

In principle, all of these components can be those which are present in a conventional ventilator 20.

An apparatus 22 for determining recruitable volume can be connected to the ventilator 20. The functions of the apparatus 22 can be implemented by a computer program on a medium which transfers the programming to the control unit 16 for performing the method steps disclosed below.

The main purpose of the apparatus 22 according to the invention is to determine the recruitable volume of a lung.

In principle this determination is made is such way that identical test breaths are provided within certain time intervals. During the test breaths volume and pressure changes in the lung are determined. This can be through direct measurement or by calculations based on measured values. Volume and pressure changes between different test breaths are then compared with respect to volume differences within a certain pressure interval.

Figure 2:
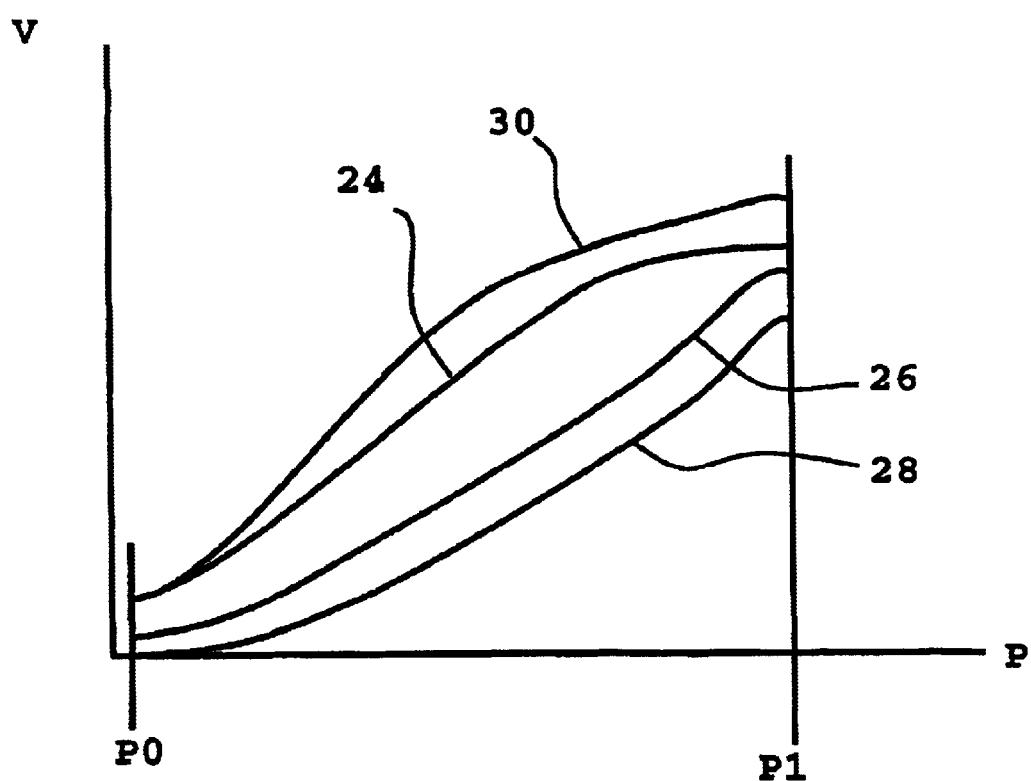
FIG. 2 is a diagram illustrating the functioning of the apparatus, using curves.

In FIG. 2 this is shown in a diagram displaying pressure and volume. A first curve 24 exemplifies a volume-pressure relationship for a first test breath. A second curve 26 represents the volume-pressure relationship during a second test breath, at a later point in time. Between selected pressure values P0 and P1 it is evident that the second curve is disposed underneath the first curve 24. For each given pressure value a smaller volume thus has entered the lung.

The average value of the volume difference between the selected pressure values P0 and P1 forms a measure of how the lung has changed between the points in time. The difference is (at least in part) caused by collapsing alveoli in the lung. The comparison thus provides a measure of the size of volume lost through collapse and thus can be viewed as being recruitable again.

The comparison also provides a measure for the progress of the treatment. Even the difference in volume at the second pressure value P1 provides information of whets happening in the lung. If the difference is reduced closer to the second pressure value P1 this is an indication that some recruition of the lung takes place toward the end of the second test breath.

The area between the first curve 24 and the second curve 26 also provides a measure of how large the portion of the lung is that has collapsed during the time period between the measurements. The treatment thus may require a change if the portion (area) is too large. The portion is thus also a measurement of how large recruitable volume there is.

A third curve 28 displays the situation at a third point in time. From the comparison a certain amount of continuing collapse can be established and this without any recruitment during the test breath. the difference in area between the second curve 26 and the third curve 28 is, however, less than corresponding difference between the first curve 24 and the second curve 26 (the same is valid for the volume differences).

A fourth curve 30 has also been marked in order to illustrate that continuing recruitment of the lung may take place, resulting in an increased volume.

An increase of this kind means that a major improvement has occurred in the lung in that previously non-recruited areas have become recruitable or that recruitable area has gained an improved elasticity and ventilation.

The determination of flow/volume and pressure preferably takes place as close as possible to the lung. This has been illustrated in FIG. 1 with a pressure and flow meter 32 adapted for bronchial placement, below the patient connector 10 in the patient 12. The pressure and flow meter 32 is here shown as being directly connected to the apparatus 22.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for determining a recruitable volume in a lung comprising:

a pneumatic unit adapted to interact with a respirating subject for supplying a breathing gas flow to the subject;

a measurement system adapted to interact with the subject for measuring volume and pressure associated with respiration; and a control system connected to said pneumatic unit and to said measurement system, said control system operating said pneumatic unit mode applying elevated pressure to a lung of the subject, at a first point in time, regulating the pneumatic unit to generate a first test breath having predetermined parameters with respect to at least one of flow and pressure of the breathing gas flow, and registering volume and pressure in the lung during the first test breath, measured by the measurement system, at a second point in time, and regulating the pneumatic unit to generate a second test breath identical to the first test breath, and registering volume and pressure in the lung during the second test breath, measured by the measurement system, comparing the registered volume and pressure for each of the first test breath and the second test breath, and determining a recruitable volume and assessing an efficacy of said elevated pressure based on the comparison.

2. An apparatus according to claim 1 wherein the control system operates for, at a $n^{th}$ point in time, regulating the pneumatic unit to generate an $n^{th}$ test breath identical to the first test breath, n being an integer equal to or greater than 3, and for registering volume and pressure in the lung during the $n^{th}$ test breath, measured by the measurement system, and for comparing the registered volume and pressure in the lung for the $n^{th}$ test breath and preceding test breaths, and for determining a trend for changes in said recruitable volume based on the comparison.

* * * * *